United States Patent
Hyun et al.

(10) Patent No.: US 11,040,125 B2
(45) Date of Patent: Jun. 22, 2021

(54) NEUROTROPHIC FACTOR CARRIER, METHOD FOR PRODUCING THE SAME, AND METHOD FOR REGENERATING A NERVE USING THE SAME

(71) Applicant: Wiregene Co., Ltd., Chungcheongnam-do (KR)

(72) Inventors: Jung Keun Hyun, Chungcheongnam-do (KR); Jong-Wan Kim, Chungcheongnam-do (KR); Jun-Hyeog Jang, Incheon (KR); Min Soo Kim, Chungcheongnam-do (KR); Hong Sun Ahn, Chungcheongnam-do (KR)

(73) Assignee: Wiregene Co., Ltd., Chungcheongnam-do (KR)

( * ) Notice: Subject to any disclaimer, the term of this patent is extended or adjusted under 35 U.S.C. 154(b) by 0 days.

(21) Appl. No.: 15/797,012

(22) Filed: Oct. 30, 2017

(65) Prior Publication Data
US 2018/0133373 A1 May 17, 2018

(30) Foreign Application Priority Data

Nov. 17, 2016 (KR) .................. 10-2016-0153484
Oct. 26, 2017 (KR) .................. 10-2017-0140474

(51) Int. Cl.
| | | |
|---|---|---|
| *A61L 27/56* | (2006.01) | |
| *A61L 27/18* | (2006.01) | |
| *A61L 27/54* | (2006.01) | |
| *A61K 38/18* | (2006.01) | |
| *A61L 27/34* | (2006.01) | |
| *A61L 27/58* | (2006.01) | |
| *A61K 31/727* | (2006.01) | |

(52) U.S. Cl.
CPC ............ *A61L 27/56* (2013.01); *A61K 31/727* (2013.01); *A61K 38/185* (2013.01); *A61L 27/18* (2013.01); *A61L 27/34* (2013.01); *A61L 27/54* (2013.01); *A61L 27/58* (2013.01); *A61L 2300/414* (2013.01); *A61L 2300/42* (2013.01); *A61L 2300/602* (2013.01); *A61L 2430/32* (2013.01)

(58) Field of Classification Search
CPC .......... A61L 27/56; A61L 27/18; A61L 27/34; A61L 27/54; A61L 27/58; A61K 31/727; A61K 38/185
See application file for complete search history.

(56) References Cited

U.S. PATENT DOCUMENTS

| | | | |
|---|---|---|---|
| 2003/0176876 A1* | 9/2003 | Chen | A61B 17/1128 606/152 |
| 2005/0232970 A1* | 10/2005 | Stucke | A61K 31/4745 424/426 |
| 2010/0076465 A1* | 3/2010 | Wiberg | A61B 17/1128 606/152 |
| 2011/0033504 A1* | 2/2011 | Wheatley | A61K 35/28 424/400 |

FOREIGN PATENT DOCUMENTS

| | | | |
|---|---|---|---|
| CN | 104208746 | * | 12/2014 |
| KR | 10-2015-0105826 | | 9/2015 |
| KR | 2015/0105826 | * | 9/2015 |
| WO | WO 2016/138701 | * | 9/2016 |

OTHER PUBLICATIONS

Zhongyang et al. (CN 104208746; published: Dec. 17, 2014); English machine translation obtained on Jun. 13, 2019.*
Keun et al. (KR 2015/0105826; published: Sep. 18, 2015); English machine translation obtained on Jun. 13, 2019.*
Liu et al., WO 2016/138701, published: Sep. 9, 2016, English machine translation obtained on Aug. 3, 2020. (Year: 2020).*

* cited by examiner

*Primary Examiner* — Genevieve S Alley

(57) ABSTRACT

The present invention relates to a neurotrophic factor carrier, particularly to a neurotrophic factor carrier wherein the neurotrophic factor is contained in a porous nerve conduit having micropores formed in microchannels, a method for preparing the same and a method for regenerating a nerve using the same, wherein the neurotrophic factor carrier prepared according to the present invention is applicable to in-vitro and in-vivo researches on nerves.

8 Claims, 12 Drawing Sheets
Specification includes a Sequence Listing.

SDS-PAGE

SDS-PAGE

Scale bars = 500 um

NEUROTROPHIC FACTOR CARRIER, METHOD FOR PRODUCING THE SAME, AND METHOD FOR REGENERATING A NERVE USING THE SAME

CROSS-REFERENCE TO RELATED APPLICATION

This application claims priority of Korean Patent Application No. 10-2016-0153484, filed on Nov. 17, 2016, and priority of Korean Patent Application No. 10-2017-0140474, filed on Oct. 26, 2017, in the KIPO (Korean Intellectual Property Office), the disclosure of which is incorporated herein entirely by reference.

BACKGROUND OF THE INVENTION

Field of the Invention

The present invention relates to a neurotrophic factor (NTF) carrier, particularly to a neurotrophic factor carrier wherein a neurotrophic factor is contained in a porous nerve conduit having micropores formed in microchannels, a method for preparing the same and a method for regenerating a nerve using the same.

Description of the Related Art

When a peripheral nerve is damaged due to injury, the sections of the cut nerve are connected with each other directly. However, such anastomosis is almost impossible for most nerves. In this case, autologous nerve grafting is conducted to restore its function. However, the autologous nerve grafting is problematic in that it is difficult to match the thickness and shape of the nerve tissue of the damaged area and the grafted nerve tissue, the nerves that can be taken for the grafting are limited and the decline in function can occur at the area where the grafted nerve is taken. Therefore, a nerve conduit is used to restore the function of a damaged nerve.

The nerve conduit connects both ends of the damaged nerve and serves as a means of guiding nerve regeneration. The both ends of the damaged nerve are fixed inside the nerve conduit to induce the connection of the nerve in the conduit. When the nerve conduit is used, it is advantageous in that the infiltration of scar tissue interfering with nerve regeneration can be prevented, nerve regeneration can be induced along a desired direction, the nerve regeneration promoting substances secreted from the nerve itself is maintained inside the conduit and the substances interfering with the regeneration can be blocked.

The nerve conduit should be biocompatible to avoid tissue rejection and should be biodegraded after nerve regeneration so that the removal of the nerve conduit is unnecessary after the nerve regeneration. Also, the degradation product of the nerve conduit should be nontoxic in the body.

In addition, the nerve conduit should have the mechanical property necessary to maintain the inside space during the nerve regeneration. The nerve conduit should have suitable flexibility and tensile strength so that the end portion of the nerve conduit can be maintained stably after the insertion of the nerve conduit. Also, the nerve conduit should be able to prevent damage to nearby normal tissues and should be easily transplantable.

As the material of the nerve conduit, natural polymers such as collagen, chitosan, etc. and synthetic polymers such as silicone, polylactic acid (PLA), polyglycolic acid (PGA), poly(lactic-co-glycolic acid) (PLGA), polycaprolactone, etc. are available.

Among them, collagen is the most frequently used natural polymer material. Collagen has been frequently used as the material of the nerve conduit for nerve regeneration due to excellent biocompatibility and weak antigenicity. However, the use of collagen is problematic in that it has to be extracted from an animal, storage is complicated and large-scale production is difficult. Also, it costs a lot to prepare the nerve conduit using collagen. In addition, the nerve conduit prepared from collagen is limited in clinical application because of weak tensile strength.

The synthetic polymers such as PLA, PLGA, etc. have been verified to be biocompatible. A nerve conduit based on these synthetic polymers has superior structural stability and tensile strength because is formed as a tube without pores (small holes). However, the synthetic polymer-based nerve conduit is problematic in that control of physical properties is difficult. In addition, the synthetic polymer-based nerve conduit known thus far is disadvantageous in that the exchange of body fluid is not achieved easily.

Korean Patent Application No. 2014-0027854 discloses a method for preparing a synthetic polymer-based nerve conduit using glass fibers. However, the nerve conduit still has the problem that the exchange of body fluid is difficult because it is in the form of a polymer tube without pores.

As described above, the nerve conduit is prepared from a biodegradable material. It is necessary to measure the time required for degradation of the biodegradable material. In general, the biodegradation of the biodegradable nerve conduit prepared from the biomaterial is determined by measuring weight change.

However, the weight of the biomaterial varies greatly depending on the moisture remaining in the material. For a nerve conduit having an internal structure, additional data are required regarding how the initial internal structure is changed as the nerve conduit is degraded. However, such information is not enough.

In order to solve these problems, the inventors of the present invention have researched on a porous nerve conduit having microchannels and micropores at the same time and have completed the present invention. The inventors of the present invention have also researched on a nerve conduit containing a neurotrophic factor and have completed the present invention.

SUMMARY OF THE INVENTION

The present invention is directed to providing a method for preparing a neurotrophic factor carrier.

The present invention is also directed to providing a neurotrophic factor carrier prepared by the preparation method.

The present invention is also directed to providing a method for regenerating a nerve.

The present invention provides a method for preparing a neurotrophic factor carrier, including: a step of preparing a polymer material for a nerve conduit by dissolving a hydrophobic biocompatible polymer in a water-miscible organic solvent; a step of preparing a nerve conduit formed of a porous polymer having micropores formed in microchannels of the hydrophobic polymer by immersing the polymer material for a nerve conduit in a hydrophilic solution and thereby separating the organic solvent from the polymer material; a step of modifying the surface of the porous nerve conduit with an amine group or immersing the porous nerve conduit in a heparin solution; and a step of immersing the porous nerve conduit in a neurotrophic factor solution.

That is to say, in the present invention, the "neurotrophic factor carrier" refers to a porous nerve conduit containing a neurotrophic factor.

The neurotrophic factor carrier may be for regeneration of a central nerve or a peripheral nerve.

The nervous system of higher animals is classified into the central nervous system, the peripheral nervous system and the autonomic nervous system. The central nervous system is a nervous system including the brain and the spinal cord. The peripheral nervous system is a nervous system which diverges from the central nervous system such as the brain and spinal cord and is distributed throughout the body like branches.

In general, when the axon of the neuron constituting the peripheral nervous system is physically damaged, it regenerates normally and restores its function with time. However, when the peripheral nerve is damaged due to accidents, surgery, etc., social activities may be severely affected. In particular, when the nerves of the hands or feet are cut, it is difficult to connect them. For the central nervous system, neuronal damage leads to permanent loss of function.

When the peripheral nerve is cut, the cut nerve grows at the peripheral site at a speed of about 1 mm per day. Therefore, the cut nerve can be regenerated by introducing a tube-type nerve conduit to the cut site.

The nerve conduit serves as a passage for connecting the broken nerve tissue and regenerating nerve fibers. Accordingly, when both ends of the cut nerve are connected to the nerve conduit, the nerve may be regenerated as nerve fiber grows at one side of the nerve inside the nerve conduit. In addition, the nerve conduit provides a controlled microenvironment and the growth of axon may be promoted as neurotrophic factors secreted from the damaged nerve are concentrated in the conduit.

It is known that the central nerve such as the spinal cord, etc. cannot be regenerated once it is damaged by injury such as a traffic accident or by cerebrovascular accident, which is contrasted with the peripheral nerve. Because the central nerve cannot be regenerated once it is damaged, the damage to the central nerve often leads to partial or complete paralysis.

The damaged central nerve can be regenerated by using the nerve conduit. An example is as follows. When both ends of a damaged spinal nerve are connected by the nerve conduit, the central nerve may be regenerated as the nerve grows inside the nerve conduit. A nerve conduit having micropores as in the present invention facilitates the growth of axon because the neurotrophic factors secreted from the damaged nerve are secreted well inside the nerve conduit too. In particular, the nerve conduit according to the present invention allows easy nerve generation by containing a neurotrophic factor.

Accordingly, the porous nerve conduit containing the neurotrophic factor, i.e., the neurotrophic factor carrier, of the present invention allows nerve generation by using the neurotrophic factor carrier only without the need of additionally administering cells or drugs that help nerve regeneration. Regeneration of the peripheral nerve or the central nerve is possible by using the neurotrophic factor carrier of the present invention. Although it is known that the regeneration of the central nerve is almost impossible, not only the peripheral nerve but also the central nerve can be regenerated by using the neurotrophic factor carrier of the present invention.

In the present invention, the term "hydrophobic biocompatible polymer" refers to a polymer which is biocompatible, biodegradable and insoluble in water.

As the hydrophobic biocompatible polymer, any hydrophobic biocompatible polymer commonly used in the related art may be used without limitation. Specifically, one or more selected from a group comprising of polylactic acid (PLA), poly-L/D-lactide (PLDA), poly-L-lactic acid (PLLA), polyglycolic acid (PGA)), polydioxanone, polyhydroxybutyrate (PHB), polyhydroxyalkanoate (PHA), poly(lactic-co-glycolic acid) (PLGA), polycaprolactone (PCL), a copolymer thereof and a mixture thereof may be used, although not being necessarily limited thereto.

In the present invention, the term "water-miscible organic solvent" refers to an organic solvent which is miscible at least partly with water or completely with water.

As the water-miscible organic solvent, any water-miscible organic solvent used in the related art may be used without limitation. Specifically, it may be selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof, although not being necessarily limited thereto. More specifically, it may be N-methyl-2-pyrrolidone, tetraglycol or dimethyl sulfoxide, although not being necessarily limited thereto.

The "polymer material" refers to a hydrophobic biocompatible polymer dissolved in a water-miscible solvent.

In an exemplary embodiment of the present invention, a PLGA-TG or PCL-TG solution prepared by using poly (lactic-co-glycolic acid) (PLGA) or polycaprolactone (PCL) as the hydrophobic biocompatible polymer and tetraglycol (TG) as the water-miscible solvent is used as the polymer material. In particular, when the polymer material is prepared by mixing PLGA with TG, it is advantageous in that a process of dissolving the polymer material again can be omitted because a solution state is maintained at room temperature after the PLGA is dissolved with the TG.

By immersing the polymer material for a nerve conduit in the hydrophilic solution and thereby separating the organic solvent from the polymer material, a nerve conduit formed of a porous hydrophobic polymer having micropores formed may be obtained.

A detailed description is given as follows. When the polymer material for a nerve conduit formed of the hydrophobic biocompatible polymer and the water-miscible organic solvent is immersed in the hydrophilic solution, micropores are formed in the polymer as the organic solvent is released from the polymer, i.e., as the organic solvent is phase-separated.

In the present invention, the hydrophilic solution includes water, although not being limited thereto.

In the present invention, the term "micropore" refers to a very small nano-sized hole. In the present invention, the micropore refers to a very small nano-sized hole with a size of 1 μm or smaller.

The polymer material for a nerve conduit may be one in which the hydrophobic biocompatible polymer is dissolved in the water-miscible organic solvent at a concentration of 10-40 weight/volume % (w/v %), specifically 10-25 w/v %, more specifically 15-25 w/v %, most specifically 20 w/v %.

The term "weight/volume % (w/v %)" refers to the weight (g) of the hydrophobic polymer dissolved in 100 mL of the organic solvent.

If the concentration is below 10 w/v %, porosity may increase due to the excessive use of the water-miscible organic solvent. And, if the concentration exceeds 40 w/v %, enough micropores may not be formed.

In the step of modifying the surface of the porous nerve conduit with an amine group or immersing the porous nerve conduit in a heparin solution, the neurotrophic factor is coated on the surface of the nerve conduit as the amine group on the surface of the porous nerve conduit modified with the amine group is covalently bonded to the carboxyl group of the neurotrophic factor or the neurotrophic factor is coated on the surface of the nerve conduit immersed in the heparin solution as the sulfate (O-sulfate or N-sulfate) present in the heparin is ionically bonded to the lysine/ arginine of the neurotrophic factor.

The neurotrophic factor solution may be prepared to a concentration of 0.1-1000 μg/mL by mixing the neurotrophic factor with distilled water.

When the concentration of the neurotrophic factor is higher than the above range, the neurotrophic factor may not be released in a sustained manner due to excessive coating. And, when it is lower than the above range, the release amount of the neurotrophic factor may be not enough for nerve regeneration.

In an exemplary embodiment of the present invention, the neurotrophic factor is coated on the surface of the nerve conduit formed of the porous polymer having micropores formed in microchannels by immersing the nerve conduit in the heparin solution and then in the neurotrophic factor solution. The amount of the coated neurotrophic factor is about 1 mg.

The neurotrophic factor may be or may be selected from a group comprising of NT-3 (neurotrophin-3), NT-4 (neurotrophin-4), BDNF (brain-derived neurotrophic factor), NGF (nerve growth factor), GDNF (glial-derived neurotrophic factor), CNTF (ciliary neurotrophic factor) and a mixture thereof.

The neurotrophic factor may be a wild-type or recombinant neurotrophic factor.

The recombinant neurotrophic factor may be a recombinant neurotrophic factor wherein a fluorescent protein is bound to the 3' end of the neurotrophic factor.

The term "fluorescent protein" refers to a protein which emits light in vivo and thus allows to observe how proteins function in vivo. When the fluorescent protein is bound to the gene of a target protein and then injected it into a cell, the location of the protein, the growth and motion of the cell, etc. can be easily monitored due to the fluorescent protein.

In the present invention, any fluorescent protein known in the art may be used without limitation. For example, GFP (green fluorescent protein), RFP (red fluorescent protein), CFP (cyan fluorescent protein) or YFP (yellow fluorescent protein) may be used.

The term "recombinant" indicates a cell which replicates a heterogeneous nucleotide or expresses the nucleotide a peptide, a heterogeneous peptide or a protein encoded by the heterogeneous nucleotide. A recombinant cell can express a gene or a gene fragment that is not found in natural state in the form of a sense or antisense. In addition, a recombinant cell can express a gene that is found in natural state, provided that the gene is modified and re-introduced into the cell by an artificial means.

The term "vector" is used to refer to a DNA fragment(s) and a nucleotide molecule delivered into a cell. The vector can replicate a DNA and can be reproduced independently in a host cell. The term "expression vector" is frequently used interchangeably with "recombinant vector". The term "expression vector" refers to recombinant DNA molecule containing a desired coding sequence and a specific nucleotide sequence essential for expressing the coding sequence that is operably linked in a specific host organism. The expression vector constructed in the present invention may be one in which nucleotide sequences encoding the neurotrophic factor and the fluorescent protein described above are inserted and operably linked to the expression control sequence.

The expression "operably linked" means that a nucleotide fragment is linked to another nucleotide fragment such that its function or expression is affected by another nucleotide fragment. And, the "expression control sequence" refers to a DNA sequence that controls the expression of a nucleotide sequence operably linked in a specific host cell. The control sequence includes a promoter sequence for initiating transcription, an operator sequence for controlling transcription, a sequence coding for the ribosome binding site of an mRNA and a sequence controlling the termination of transcription and translation. In general, the expression vector includes an expression construct of a promoter-gene-transcription termination sequence and promoter, enhancer, termination and polyadenylation sequences that can be used are known.

The vector that can be used in the present invention may be constructed from a plasmid (e.g., pBAD, pSC101, ColE1, pBR322, pUC8/9, pHC79, pGEX series, pET series, pUC19, etc.), a phage (e.g., gt4xue, -Charon, z1, M13, etc.) or a virus (e.g., adenovirus, SV40, etc.) commonly used in the art.

The vector of the present invention can be constructed using a prokaryotic cell or a eukaryotic cell as a host. For example, when the recombinant vector of the present invention is an expression vector and a prokaryotic cell is used as a host, the vector usually contains a strong promoter capable of initiating transcription (e.g., pL promoter, trp promoter, lac promoter, T7 promoter, tac promoter, etc.), a ribosome binding site for initiating translation and a transcription/ translation termination sequence. The term "promoter" to a DNA molecule to which RNA polymerase binds to initiate transcription. It corresponds to a DNA region upstream of a structural gene.

In the expression vector of the present invention, the promoter may be any of CaMV 35S, actin, ubiquitin, pEMU, MAS or histone promoters, although not being limited thereto. Specifically, in the present invention, the promoter contained in the expression vector may be one having a strong expression ability.

Specifically, the expression vector of the present invention may be one for use in bacteria and may contain a promoter sequence and a nucleotide sequence of a gene to be expressed (neurotrophic factor and fluorescent protein). These sequences may be connected in the 5'-3' direction.

The expression vector constructed in the present invention is constructed so as to express a desired gene in a host cell.

The expression vector of the present invention may contain an antibiotic-resistant gene commonly used in the art as a selection marker. For example, genes resistant to ampicillin, gentamicin, carbenicillin, chloramphenicol, streptomycin, kanamycin, geneticin, neomycin and tetracycline may be used.

In the present invention, the expression vector may be introduced into a host cell by a method known in the art. For example, a method of preparing a competent cell using a $CaCl_2$ buffer and then introducing the expression vector into a host cell by applying a heat shock (42° C.), electric shock-mediated transfection, transient transfection, microinjection, cell fusion, calcium phosphate transfection, electroporation, etc. may be used, although not being limited thereto. Specifically, electric shock-mediated transfection may be employed for stable and effective preparation of a transformant.

In the present invention, a wild-type bacterial species which is industrially applicable and exhibits superior functionality is used as the host cell. The wild-type species can be selected by comparing the characteristics of the bacteria in the Gram-negative genus *Escherichia*. The bacteria in the genus *Escherichia* may include *Escherichia coli* TOP10, MG1655, W3110, DH5α, XL1-Blue and BL21. Specifically, *E. coli* TOP10 may be used.

In an exemplary embodiment of the present invention, the cDNA of the human neurotrophic factor is amplified by PCR and then cloned into the expression vector pBAD-HisA. Then, by amplifying the cDNA of the fluorescent protein by PCR and cloning the same into the expression vector pBAD-HisA containing the cDNA of the human neurotrophic factor, an expression vector for expressing the recombinant neurotrophic factor conjugated with the fluorescent protein is constructed. The constructed expression vector is introduced into *E. coli* TOP10 by the heat shock method, so that the recombinant neurotrophic factor is produced in large scale in the *E. coli*. The produced recombinant neurotrophic factor is purified to a purity of 95% or higher by affinity chromatography.

The term "PCR (polymerase chain reaction)" refers to a technique of amplifying a target nucleotide from a primer pair binding specifically to the target nucleotide using a polymerase. The PCR method is well known in the art and a commercially available kit may be used.

The term "primer" refers to a short nucleotide sequence having a free 3'-hydroxyl group, which can form a base pair with a complimentary nucleotide template and serves as a starting point for replication of the nucleotide template. The primer can initiate DNA synthesis in a suitable buffer at a suitable temperature in the presence of a polymerase (i.e., a DNA polymerase) and reagents for polymerization.

Specifically, the expression vector according to the present invention contains an ampicillin-resistant gene and has the neurotrophic factor gene upstream of the 5' end of the fluorescent protein gene, although not being limited thereto. More specifically, it may be a pBAD-HisA-BDNF-GFP vector (FIG. 10), a pBAD-HisA-NGF-RFP vector (FIG. 12), a pBAD-HisA-GDNF-GFP vector or a pBAD-HisA-CNTF-GFP vector, although not being limited thereto.

The nerve conduit formed of a porous polymer, having micropores formed in microchannels, may be prepared by a method including: a step of inserting a plurality of glass fibers into a container having upper and lower channels; a step of injecting a polymer material for a nerve conduit containing a hydrophobic biocompatible polymer and a water-miscible organic solvent into the container in which the plurality of glass fibers are inserted; a step of infiltrating the polymer material between the glass fibers by applying vacuum to the upper channel; a step of separating the glass fibers with the polymer material infiltrated from the container; and a step of dissolving the glass fibers by immersing the separated glass fibers in a hydrophilic solution, wherein the polymer material for a nerve conduit is one in which the hydrophobic biocompatible polymer is dissolved in the water-miscible organic solvent at a concentration of 10-40 weight/volume % (w/v %) and, in the step of dissolving the glass fibers, microchannels are formed as the hydrophobic biocompatible polymer is cured and micropores are formed in the microchannels formed of the hydrophobic polymer as the water-miscible organic solvent is mixed with the hydrophilic solution and released from the hydrophobic polymer.

The term "microchannel" refers to a void space with a size of 5-20 μm formed as the glass fibers are dissolved and means a channel with a microstructure formed inside the nerve conduit. The microchannel guides the growth of axons along a desired direction and prevents infiltration of scar tissue which interferes with nerve regeneration. In addition, a structure capable of drug delivery, etc. may be provided by attaching neurotrophic factors, etc. to the microchannels formed inside the nerve conduit.

The nerve conduit of the present invention may have about 1,000-10,000 channels. But, it may also contain more channels.

The present invention provides a method for preparing a porous nerve conduit having micropores formed in microchannels. The processes of forming the microchannels and the micropores are described in detail as follows.

The polymer material for a nerve conduit formed of the hydrophobic biocompatible polymer and the water-miscible organic solvent is infiltrated between the space of the glass fibers filled in the container (e.g., a glass tube). Because the space between the glass fibers is narrow, the polymer material may be infiltrated by using negative pressure or positive pressure. After the polymer material is filled between the glass fibers, the glass fibers and the polymer material are separated from the container and immersed in the hydrophilic solution. Then, microchannels are formed in the space that has been occupied by the glass fibers as the glass fibers are dissolved and micropores are formed as the water-miscible organic solvent is released from the polymer material. Specifically, when the glass fibers are dissolved in the hydrophilic solution (e.g., water) and the water is contacted with the hydrophobic polymer, microchannels are formed as the polymer having hydrophobic property is cured. And, when water is introduced into the newly formed microchannels, micropores are formed as the water-miscible organic solvent is mixed with the water and released from the hydrophobic polymer, i.e., as the organic solvent is phase-separated.

The nerve conduit prepared according to the present invention allows easy body fluid exchange in vivo due to the microchannels having the micropores formed.

The lower channel may have a smaller diameter than the upper channel and the container may be sloped with a discontinuous angle.

Because the lower channel has a smaller diameter than the upper channel, the glass fibers injected into the container may remain filled inside the container without flowing out.

The container may be sloped with a discontinuous angle. More specifically, the container may have the upper and lower channels formed to be sloped with a discontinuous angle.

Due to the container sloped with a discontinuous angle and the upper and lower channels thereof, the glass fibers inserted into the container have constant intervals and the microchannels formed in the space where the glass fibers have been dissolved also have constant intervals. That is to say, because the porous nerve conduit prepared according to the present invention has microchannels formed with constant intervals, nerve regeneration can be induced along the same direction.

The upper channels and the lower channels of the container may be formed by heating the center portion of the glass tube and thereby forming a bottleneck, although not being limited thereto.

The polymer material for a nerve conduit may be in a solution state at room temperature.

In the present invention, the room temperature means a temperature of 15-25° C.

The method for preparing a neurotrophic factor carrier may further include, after the step of dissolving the glass fibers: a step of cooling a nerve conduit formed after the glass fibers are dissolved with liquid nitrogen; and a step of shaping the cooled nerve conduit by cutting.

The container may be formed of a transparent material so that the infiltration of the polymer material for a nerve conduit can be checked visually. Specifically, the transparent material may be glass, although not being necessarily limited thereto.

The application of vacuum may be repeated multiple times. Through this, a nerve conduit with a uniform density may be prepared. The application of vacuum into the container (e.g., a glass tube) may be repeated multiple times using a syringe, although not being necessarily limited thereto.

In another aspect, the present invention provides a neurotrophic factor carrier formed of a porous nerve conduit having micropores formed in microchannels, prepared by the preparation method described above.

In the neurotrophic factor carrier, the microchannels may be formed along the axis direction of the nerve conduit as the glass fibers are inserted into the container along the axis direction.

The microchannels may be formed as a polymer material for a nerve conduit formed of a water-miscible organic solvent and a hydrophobic biocompatible polymer reacts with a hydrophilic solution and the hydrophobic biocompatible polymer is cured and the micropores may be formed in the microchannels formed of the hydrophobic polymer as the water-miscible organic solvent is mixed with the hydrophilic solution and released from the hydrophobic biocompatible polymer.

The neurotrophic factor carrier may be of a sustained-release type.

The term "sustained-release type" means a dosage form designed to release a drug for a long period of time by slowing the dissolution (disintegration) of the drug and thereby slowing the absorption of the drug.

The neurotrophic factor carrier may maintain the release of the neurotrophic factor for 3-30 days.

The neurotrophic factor carrier may release 10-30 μg of the neurotrophic factor per day.

In an exemplary embodiment of the present invention, the neurotrophic factor carrier according to the present invention releases the recombinant neurotrophic factors BDNF and NGF in a sustained manner for over 30 days. In particular, after 3 days, it shows release by diffusion through the microstructure of the nerve conduit. This long-term release behavior of the neurotrophic factor for over 30 days is effective for nerve regeneration.

In an exemplary embodiment of the present invention, the neurotrophic factor carrier according to the present invention releases about 3% of recombinant BDNF and about 1% recombinant NGF per day. Considering that the initial amount of the neurotrophic factor loaded in the nerve conduit is 1 mg, the neurotrophic factor carrier exhibits a release amount of 10-30 μg, which is considered enough for nerve regeneration.

In another aspect, the present invention provides a method for regenerating a nerve by transplanting the neurotrophic factor carrier according to the present invention into a damaged nerve area.

The nerve may be a peripheral nerve or a central nerve.

Specifically, the method for regenerating a nerve may be performed by directly transplanting the neurotrophic factor carrier into a damaged nerve area or may include: a step of inserting the neurotrophic factor carrier according to the present invention into a biocompatible polymer tube formed of a hydrophobic biocompatible polymer; and a step of transplanting the biocompatible polymer tube with the neurotrophic factor carrier inserted into a damaged nerve area, wherein micropores are formed in the biocompatible tube.

The micropores may be formed in the biocompatible tube in a manner similar to the micropore preparation described above. Specifically, a glass tube is immersed in a mixture solution of a hydrophobic biocompatible polymer and a water-miscible organic solvent to form a thin coat on the surface of the glass tube. Then, when the coated glass tube is immersed in water, the hydrophobic biocompatible polymer is cured as it is contacted with water and micropores are formed in the hydrophobic polymer as the water-miscible organic solvent is mixed water and released from the hydrophobic polymer. The biocompatible tube may be obtained by pushing or pulling from the glass tube.

In an exemplary embodiment of the present invention, after inserting the glass fibers into the upper channels of the container (glass tube) along the axis direction, a polymer material (PLGA-TG solution) is injected into the container and infiltrated into the glass fibers by applying vacuum. Then, after separating the glass fibers from the container, the glass fibers are dissolved completely by immersing in water (DW). When the glass fibers are dissolved, microchannels are formed as the hydrophobic polymer is contacted with water and cured and micropores are formed in the microchannels. That is to say, the nerve conduit having microchannels with micropores formed in the axis direction is formed in the space where the glass fibers have been dissolved by inserting the glass fibers along the axis direction of the container and then dissolving the glass fibers.

And, in an exemplary embodiment of the present invention, the neurotrophic factor carrier containing the nerve conduit may be used to regenerate a peripheral nerve and/or a central nerve without the need of additional cells, drugs, etc. that help nerve regeneration.

The neurotrophic factor carrier prepared according to the present invention may be prepared to have various diameters and lengths. In addition, the diameter and the length of the neurotrophic factor carrier of the present invention may be changed as desired when preparing the neurotrophic factor carrier to be applicable to in-vitro and in-vivo researches on nerves.

The present invention provides the following effects.

According to a preparation method of the present invention, a polymer material in which a hydrophobic biocompatible polymer is dissolved in a water-miscible solvent is infiltrated between glass fibers and then immersed in a hydrophilic solution. Then, microchannels are formed as the hydrophobic polymer is contacted with the hydrophilic solution and cured, whereas micropores are formed in the hydrophobic biocompatible polymer as the water-miscible solvent is released from the polymer. The micropores allow exchange of body fluid.

As the hydrophobic biocompatible polymer is mixed with the water-miscible solvent, the melting point of the polymer solution is lowered. Therefore, after the hydrophobic biocompatible polymer is dissolved in the water-miscible solvent, the solution state is maintained at room temperature and a process of dissolving the polymer material again is unnecessary.

By infiltrating the polymer solution with a predetermined viscosity into the space between the glass fibers and repeatedly applying vacuum multiple times, a neurotrophic factor carrier with a uniform density can be prepared.

A peripheral nerve and/or a central nerve can be regenerated using the neurotrophic factor carrier according to the present invention without having to use additional cells, drugs, etc. that help nerve regeneration.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
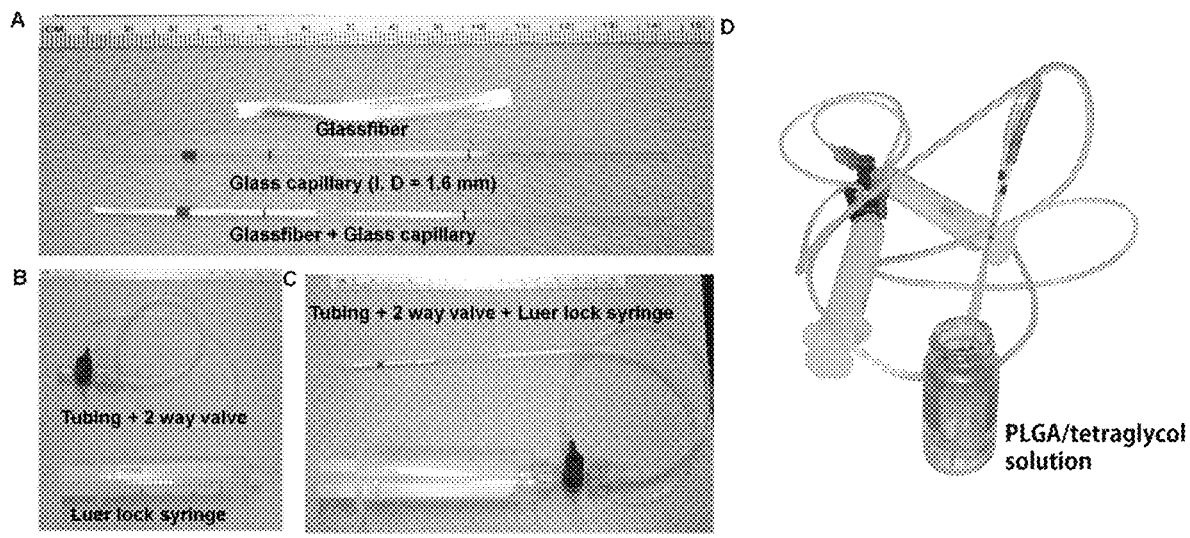
FIG. 1 shows photographs illustrating a method for preparing a porous nerve conduit. A shows glass fibers, a glass capillary and a glass capillary into which glass fibers are inserted, B shows a silicone tube coupled with a 2-way valve and a Luer lock syringe, C shows a silicone tube coupled with a 2-way valve and a Luer lock syringe, and D shows application of vacuum into a glass tube using a syringe.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Example 1

Porous Nerve Conduit Containing Nerve Growth Factor (NGF)

1-1: Preparation of Porous PLGA Nerve Conduit

A 20% (w/v) PLGA-TG solution (polymer material) was prepared by mixing the hydrophobic polymer poly(lactic acid-co-glycolic acid) (PLGA) (lactic acid/glycolic acid mol %, 85:15) and the water-miscible solvent tetraglycol (TG) (density: 1.09 g/mL, Sigma-Aldrich, USA) at a weight/volume (w/v) ratio of 20% (w/v) and then dissolving at 60° C. for 18 hours.

A glass capillary with an inner diameter of 1.6 mm and a length of 13 cm was heated at the center portion to form a bottleneck, thereby forming upper and lower channels sloped with a discontinuous angle. The lower channels were formed to have smaller diameters than the upper channel. Then, 7000-8500 strands of a water-soluble glass fiber ($50P_2O_5-20CaO-30Na_2O$ in mol % (1100° C., 800 rpm)) with diameters of 10-20 μm were cut to 5-6 cm and inserted densely into the upper channels of the glass tube along the axis direction (FIG. 1A and FIG. 2A).

A pressure device prepared by connecting a Luer lock syringe equipped with a silicone tube of an inner diameter of 0.8 mm and a length of 15 cm, coupled with a 2-way valve, to the upper channels of the glass fiber-inserted glass tube (FIG. 1B and FIG. 1C).

Figure 2:
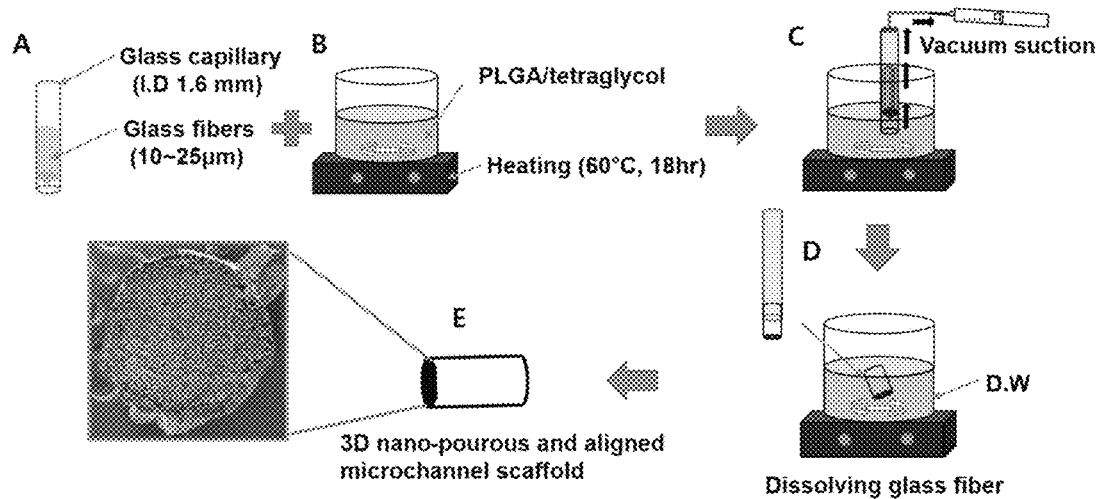
FIG. 2 schematically shows a method for preparing a porous nerve conduit.

After immersing the lower channels of the glass tube in the 20% (w/v) PLGA-TG solution at room temperature, vacuum was repeatedly applied into the glass tube using a syringe such that the 20% (w/v) PLGA-TG solution was completely infiltrated into the void space between the glass fibers (FIG. 1D and FIG. 2C).

Figure 3A:
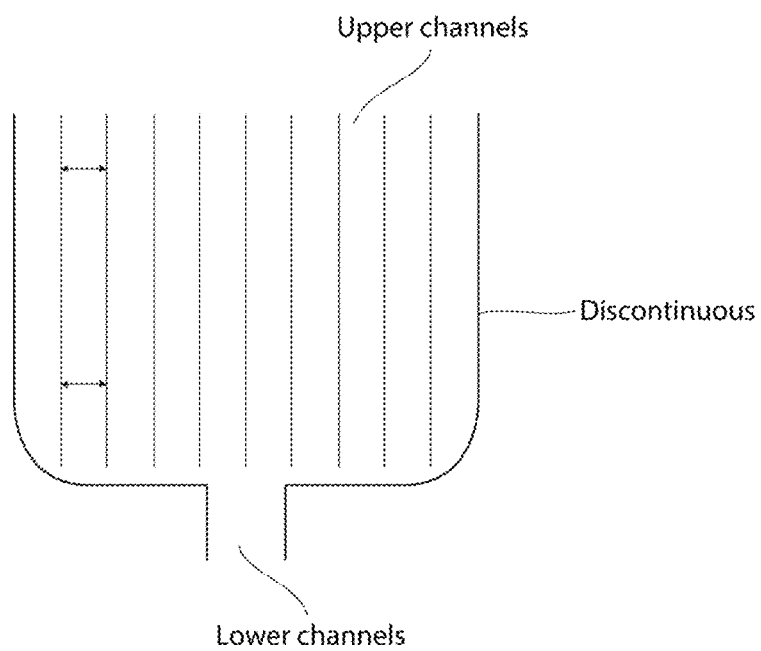
FIG. 3A and FIG. 3B show channel formation in a container with a discontinuous (A) or continuous (B) slope.
Figure 3B:
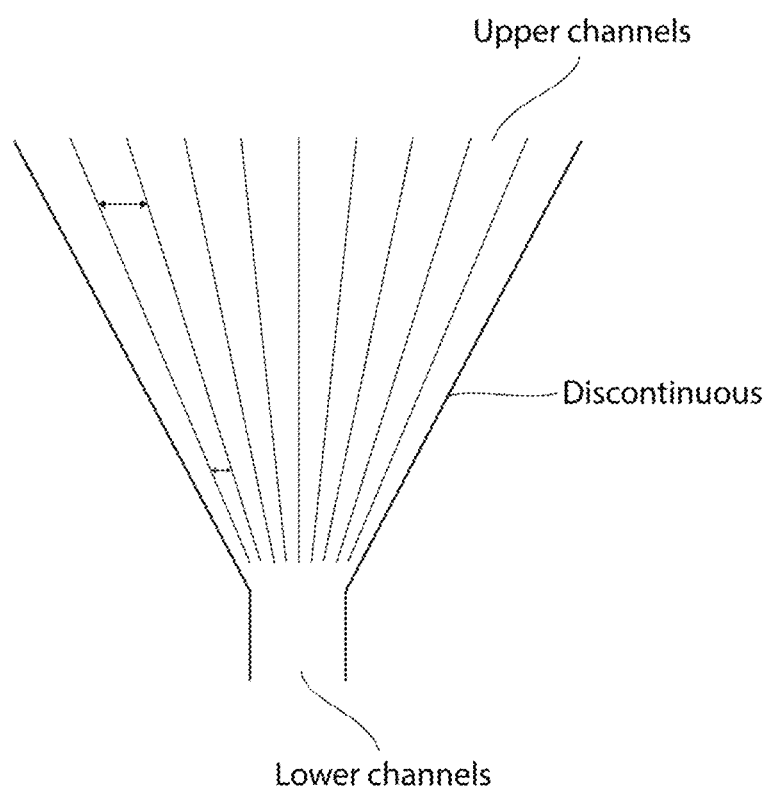

The specific configuration of the glass tube (container) is shown in FIG. 3A. As shown in FIG. 3A, the diameter of the lower channels was decreased than that of the upper channels with a discontinuous angle. If the angle is continuous (FIG. 3B), it is difficult to maintain constant intervals between the glass fibers because the intervals between the glass fibers decrease gradually.

If the nerve conduit is prepared in the state where the intervals between the glass fibers are not constant, the intervals between the microchannels of the nerve conduit will not be constant too. Then, the direction of nerve regeneration induced by the glass fibers will be different depending on the microchannel. As a result, it is difficult to induce nerve regeneration in the same direction.

Figure 4:
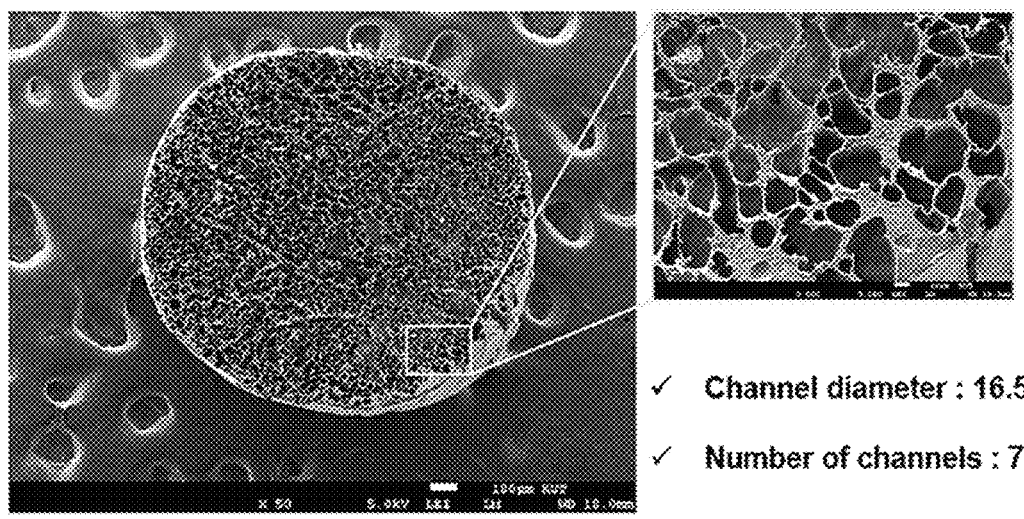
FIG. 4 shows transverse cross-sectional SEM images of a porous PLGA nerve conduit; scale bar=(left) 100 μm, (right) 10 μm.
Figure 5:
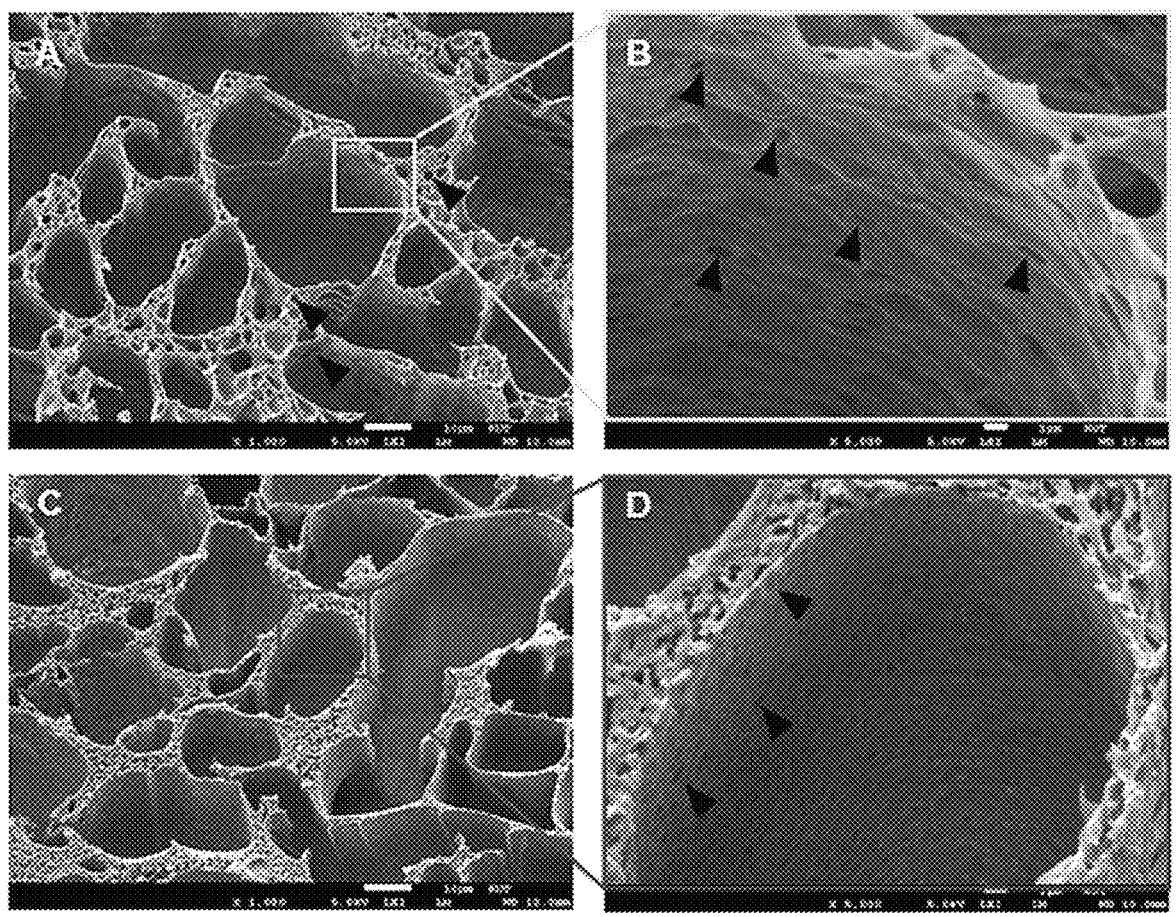
FIG. 5 shows magnified SEM images showing a microstructure at the transverse cross section of a porous nerve conduit; scale bar=(A, C) 10 μm, (B, D) 1 μm, ▶ =micropores inside microchannels.
Figure 6:
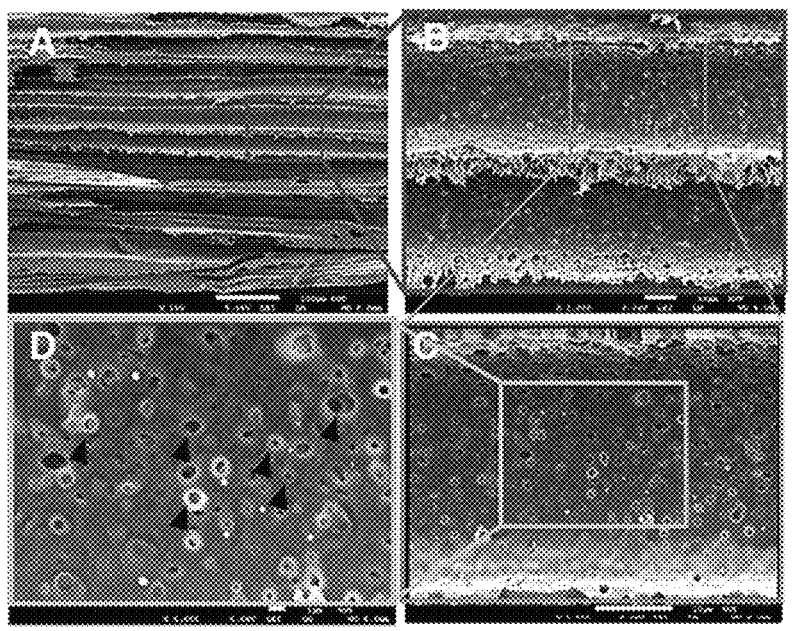
FIG. 6 shows longitudinal cross-sectional SEM images of a porous nerve conduit; scale bar=(A) 100 μm, (B) 10 μm, (C) 10 μm, (D) 1 μm, ▶ =micropores inside microchannels.
Figure 7:
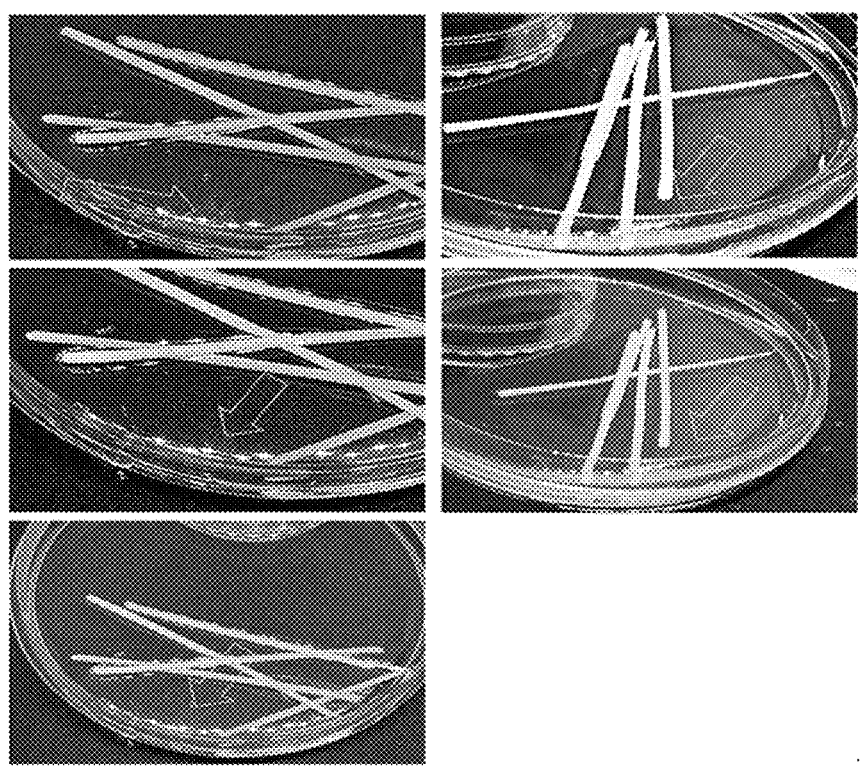
FIG. 7 shows TG released from a porous nerve conduit and submerged in distilled water (DW); arrow: TG.

The PLGA-TG solution-infiltrated glass fibers were separated from the glass tube using a wire with a diameter of 1.5 mm and a length of 15 cm and, immediately thereafter, completely immersed in distilled water (DW) at 10-20° C. for at least 24 hours (FIG. 2D), so that the glass fibers were completely dissolved, and about 7,000-8,500 (7,777±716.2) microchannels of PLGA, with diameters of 10-20 μm (16.54±3.6 μm), were formed in the space where the glass fibers had been dissolved (FIG. 2E and FIG. 4). The microchannels were formed as the glass fibers were dissolved in the water at 10-20° C. and the hydrophobic polymer PLGA was cured at the same time. Also, micropores were formed inside the microchannels as the TG was mixed with the water and released from the hydrophobic polymer while the glass fibers infiltrated with the PLGA-TG solution were immersed in the DW (FIG. 4, FIG. 5 and FIG. 6). Because the TG released from the nerve conduit had a higher density than the DW, it was submerged like heat haze in the DW (FIG. 7).

Figure 8:
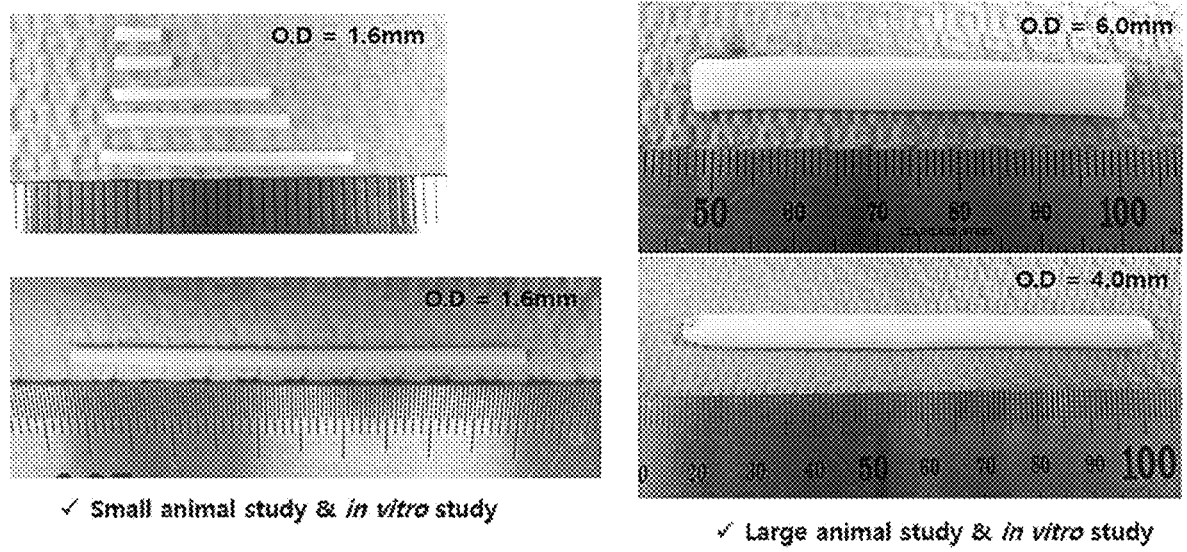
FIG. 8 shows porous nerve conduits prepared with various diameters and lengths depending on applications.

After the glass fibers and the TG were removed through the treatment with DW, the prepared porous microchannels formed of PLGA, i.e., the nerve conduit, was frozen in liquid nitrogen for about 30 seconds, cut to a desired size and then shaped into a desired shape (FIG. 8).

1-2: Investigation of Microstructure Inside Porous Nerve Conduit

The microstructure formed in the microchannels inside the nerve conduit prepared in Example 1-1 was investigated by scanning electron microscopy (SEM) (FIG. 4, FIG. 5 and FIG. 6).

FIG. 4 shows the transverse cross section of the nerve conduit, FIG. 5 shows magnified images showing the microstructure at the transverse cross section of the nerve conduit and FIG. 6 shows the longitudinal cross section of the nerve conduit. It can be seen that the microchannels were formed continuously inside the nerve conduit and micropores were formed in the microstructure.

1-3: 3D Micro-CT Imaging of Porous Nerve Conduit

Figure 9:
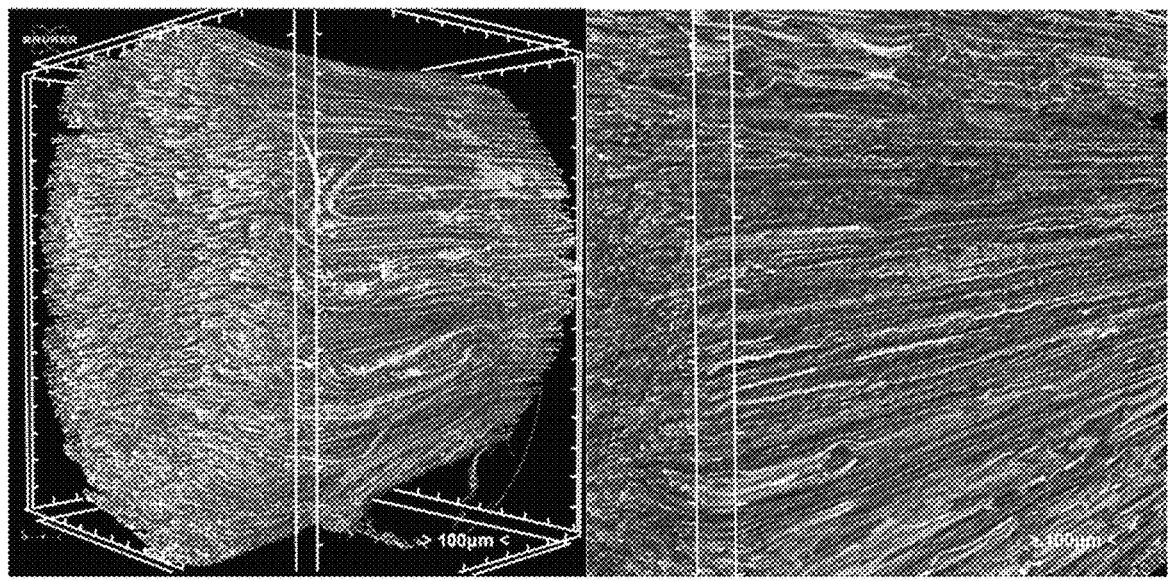
FIG. 9 shows 3D micro-CT images (sagittal plane) of a nerve conduit prepared according to an exemplary embodiment of the present invention.

The 3D CT images of the nerve conduit of Example 1-1 are shown in FIG. 9. Intact microchannels inside the nerve conduit are observed as seen from FIG. 9.

1-4: Preparation of Heparin-Coated Porous Nerve Conduit

The nerve conduit of Example 1-1 was washed with a 2 wt % NaCl aqueous solution 3 times, for 5 minutes each. After preparing a heparin solution by mixing heparin in a 2 wt % NaCl aqueous solution to a concentration of 1 mg/mL, the nerve conduit was immersed in the heparin solution at 4° C. for 3 hours. The heparin-coated nerve conduit was washed with a 2 wt % NaCl aqueous solution 3 times, for 5 minutes each. Then, the heparin-coated nerve conduit was washed with water 3 times, for 5 minutes each.

1-5: Coating of NGF on Heparin-Coated Porous Nerve Conduit

After preparing an NGF solution by mixing NGF in distilled water to a concentration of 0.1-1000 μg/mL, the heparin-coated nerve conduit of Example 1-4 was immersed in the NGF solution at room temperature for 6 hours. Then, the nerve conduit was washed with PBS (phosphate-buffered saline, pH ~7.4) 3 times, for 5 minutes each. The amount of NGF coated on the surface of the heparin-coated nerve conduit was about 1 mg.

Example 2

Recombinant Neurotrophic Factor 2-1: Large-Scale Production of Fluorescent BDNF (Brain-Derived Neurotrophic Factor)

Figure 10:
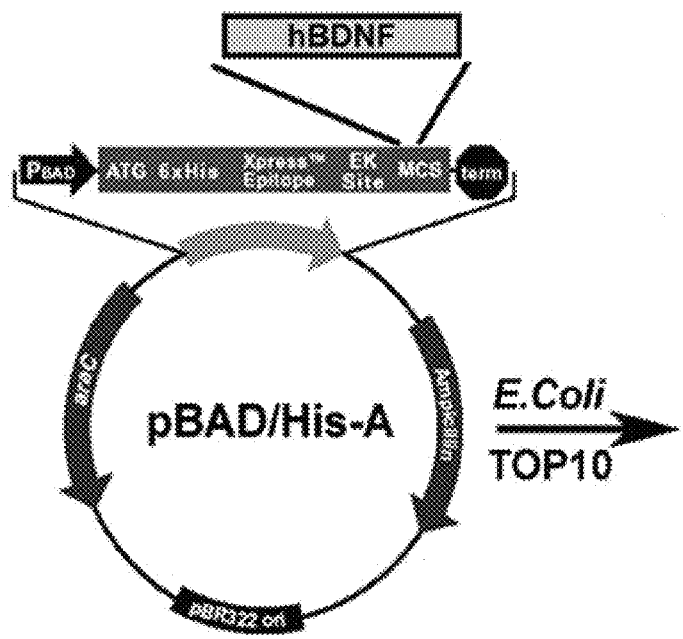
FIG. 10 schematically shows an expression vector for the recombinant neurotrophic factor BDNF.

In order to construct a recombinant fluorescent BDNF expression vector, human BDNF (hBDNF) cDNA was amplified by PCR using a forward primer 5'-GACGGTACCGCACCCATGGCAGAAGG-3' (SEQ ID NO 1) and a reverse primer 5'-AGAATTCT-CACCGCCTCGGCTTGTC-3' (SEQ ID NO 2). The PCR was performed by using 30 μL of a mixture containing 50 mM KCl, 10 mM Tris-HCl (pH 8.3), 1.5 mM MgCl2, 100 μg/mL gelatin, 0.2 mM dNTPs, 1.25 units of DNA polymerase (ELPiS Biotech, Korea) and 50 μmol of forward and reverse primers each. A cycle of annealing at 55° C. for 1 minute, extension at 72° C. for 2 minutes and denaturation at 94° C. for 1 minute was repeated 30 times. The amplification product was treated with BglII and KpnI restriction enzymes and then ligated into a pBAD-HisA vector (Invitrogen, USA) to obtain a pBAD-HisA-BDNF vector. GFP cDNA was amplified by PCR using a forward primer 5'-GGAATTCGTGAGCAAGGGCGAGGAG-3' (SEQ ID NO 3) and a reverse primer 5'-TGAATTCTACTTGTA-CAGCTCGTC-3' (SEQ ID NO 4). The amplification product was in-frame ligated into the EcoRI site of the pBAD-HisA-BDNF vector to obtain a pBAD-HisA-BDNF-GFP vector (FIG. 10).

Figure 11:
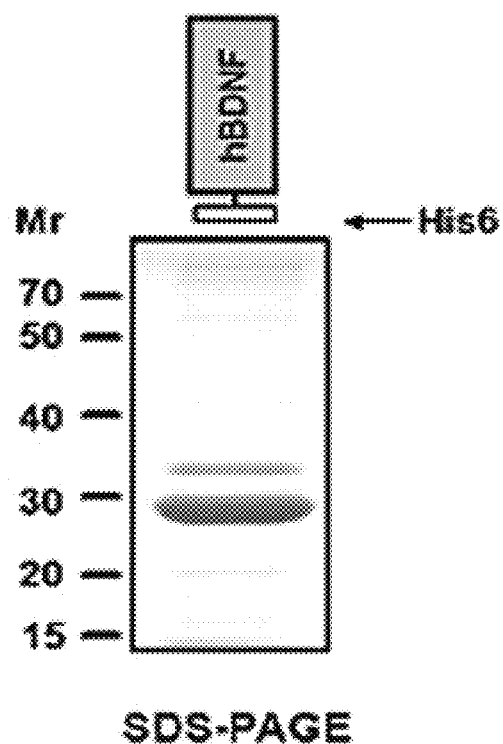
FIG. 11 shows an SDS-PAGE result for the recombinant neurotrophic factor BDNF.

For expression of a recombinant fluorescent BDNF, competent cells were prepared using a $CaCl_2$ buffer and the pBAD-HisA-BDNF-GFP vector, a recombinant fluorescent BDNF expression vector, was introduced into *Escherichia coli* TOP10 cells by applying a heat shock (42° C.). The *Escherichia coli* TOP10 cells into which the pBAD-HisA-BDNF-GFP vector was introduced were incubated overnight in an LB (Luria-Bertani) medium containing ampicillin at 37° C. When the absorbance (A600) of the medium reached 0.6, expression was induced using 0.25% (w/v) L-arabinose. 3 hours later, the culture was centrifuged and the bacteria were pelletized, lysed and then sonicated. After centrifuging at refrigerator temperature and 6,000 rpm for 30 minutes, the resulting supernatant was transferred to a fresh tube. The crude protein from the sonicated bacterial supernatant was purified to a purity of 95% or higher by affinity chromatography (ELPiS Biotech, Korea) and then analyzed by sodium dodecyl sulfate polyacrylamide gel electrophoresis (SDS-PAGE) (FIG. 11).

2-2: Large-Scale Production of Fluorescent NGF (Nerve Growth Factor)

Figure 12:
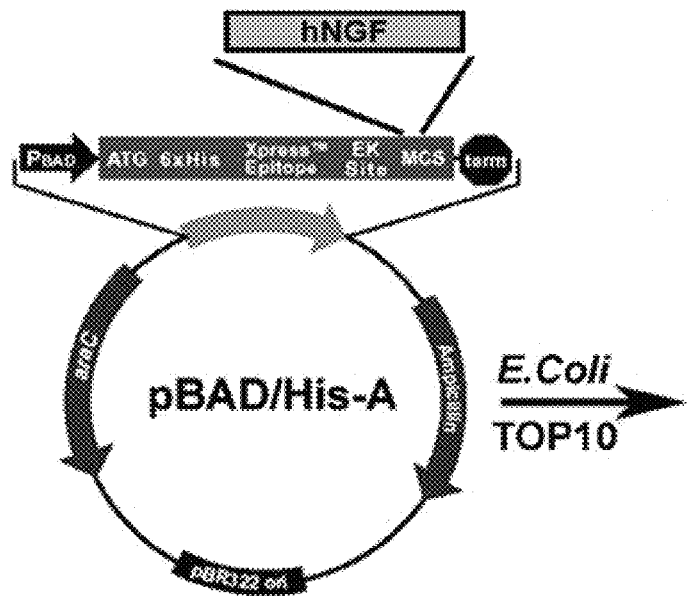
FIG. 12 schematically shows an expression vector for the recombinant neurotrophic factor NGF.

In order to construct a recombinant fluorescent NGF expression vector, human NGF (hNGF) cDNA was amplified by PCR using a forward primer 5'-GGTACCAGCAGCAGCCATCCGAT-3' (SEQ ID NO 5) and a reverse primer 5'-GAAT-TCGCCGCACGACGCACCG-3' (SEQ ID NO 6). The PCR was performed in the same manner as in Example 2-1. The amplification product was treated with KpnI and EcoRI restriction enzymes and then ligated into a pBAD-HisA vector to obtain a pBAD-HisA-NGF vector. RFP cDNA was amplified by PCR using a forward primer 5'-AAGCTTAAT-TAATTAAGTTTGTGCCCCAGTT-3' (SEQ ID NO 7) and a reverse primer 5'-AAGCTTAAT-TAAGTTTGTGCCCCAGTTTGC-3' (SEQ ID NO 8). The amplification product was in-frame ligated into the HindIII site of the pBAD-HisA-NGF vector to obtain a pBAD-HisA-NGF-RFP vector (FIG. 12).

Figure 13:
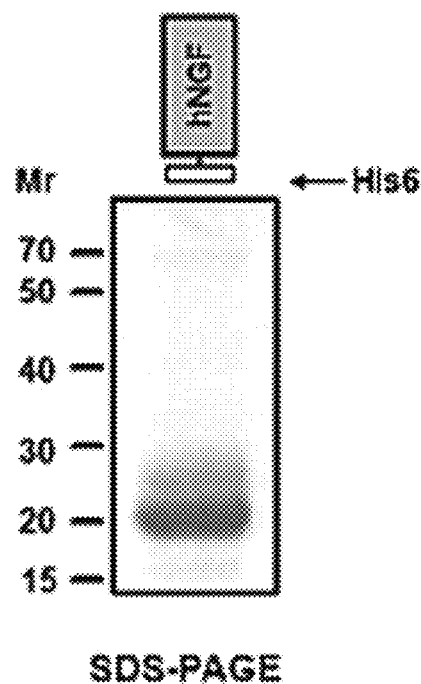
FIG. 13 shows an SDS-PAGE result for the recombinant neurotrophic factor NGF.

The recombinant fluorescent NGF was expressed in *E. coli* into which the recombinant fluorescent NGF expression vector pBAD-HisA-NGF-RFP was introduced in the same manner as in Example 2-1, which was then purified to a purity of 95% or higher and analyzed by SDS-PAGE (FIG. 13).

2-3: Large-Scale Production of Fluorescent GDNF (Glial-Derived Neurotrophic Factor)

In order to construct a recombinant fluorescent GDNF expression vector, human GDNF (hGDNF) cDNA was amplified by PCR using a forward primer 5'-GGTACCAGTCCGGATAAACAAATGGCA-3' (SEQ ID NO 9) and a reverse primer 5'-GAATTCAATACAAC-CACAACGTTTTGCG-3' (SEQ ID NO 10). The PCR was performed in the same manner as in Example 2-1. The amplification product was treated with KpnI and EcoRI restriction enzymes and then ligated into a pBAD-HisA vector to obtain a pBAD-HisA-GDNF vector. GFP cDNA was amplified by PCR using a forward primer 5'-AAGCT-TAATTAATTAAGTTTGTGCCCCAGTT-3' (SEQ ID NO 3) and a reverse primer 5'-AAGCTTAAT-TAAGTTTGTGCCCCAGTTTGC-3' (SEQ ID NO 4). The amplification product was in-frame ligated into the EcoRI site of the pBAD-HisA-GDNF vector to obtain a pBAD-HisA-GDNF-GFP vector.

The recombinant fluorescent GDNF was expressed in *E. coli* into which the recombinant fluorescent GDNF expression vector pBAD-HisA-GDNF-GFP was introduced in the same manner as in Example 2-1, which was then purified to a purity of 95% or higher and analyzed by SDS-PAGE.

2-4: Large-Scale Production of Fluorescent CNTF (Ciliary Neurotrophic Factor)

In order to construct a recombinant fluorescent CNTF expression vector, human CNTF (hCNTF) cDNA was amplified by PCR using a forward primer 5'-GGTACCG-CATTTACCGAACATAGTCCG-3' (SEQ ID NO 11) and a reverse primer 5'-GAATTCCAT-TTTTTTGTTGTTGGCAATATAATGG-3' (SEQ ID NO 12). The PCR was performed in the same manner as in Example 2-1. The amplification product was treated with KpnI and EcoRI restriction enzymes and then ligated into a pBAD-HisA vector to obtain a pBAD-HisA-CNTF vector. GFP cDNA was amplified by PCR using a forward primer 5'-AAGCTTAATTAATTAAGTTTGTGCCCCAGTT-3' (SEQ ID NO 3) and a reverse primer 5'-AAGCTTAAT-TAAGTTTGTGCCCCAGTTTGC-3' (SEQ ID NO 4). The amplification product was in-frame ligated into the EcoRI site of the pBAD-HisA-CNTF vector to obtain a pBAD-HisA-CNTF-GFP vector.

The recombinant fluorescent CNTF was expressed in *E. coli* into which the recombinant fluorescent CNTF expression vector pBAD-HisA-CNTF-GFP was introduced in the same manner as in Example 2-1, which was then purified to a purity of 95% or higher and analyzed by SDS-PAGE.

Example 3

Monitoring of Neurotrophic Factor Release Behavior

Nerve conduits with the recombinant neurotrophic factors BDNF and NGF of Example 2 coated on the surface were prepared according to the method of Example 1-5.

Then, the release behavior of the neurotrophic factors in vitro was investigated by measuring the release of the neurotrophic factors from the nerve conduits in PBS buffer. The fluorescence-labeled recombinant neurotrophic factors were quantitated by using a fluorescence microscope and the release amount was analyzed by collecting solutions at predetermined time. The release amount was calculated as a percentage of the initial coating amount 1 mg in the carrier.

Figure 14:
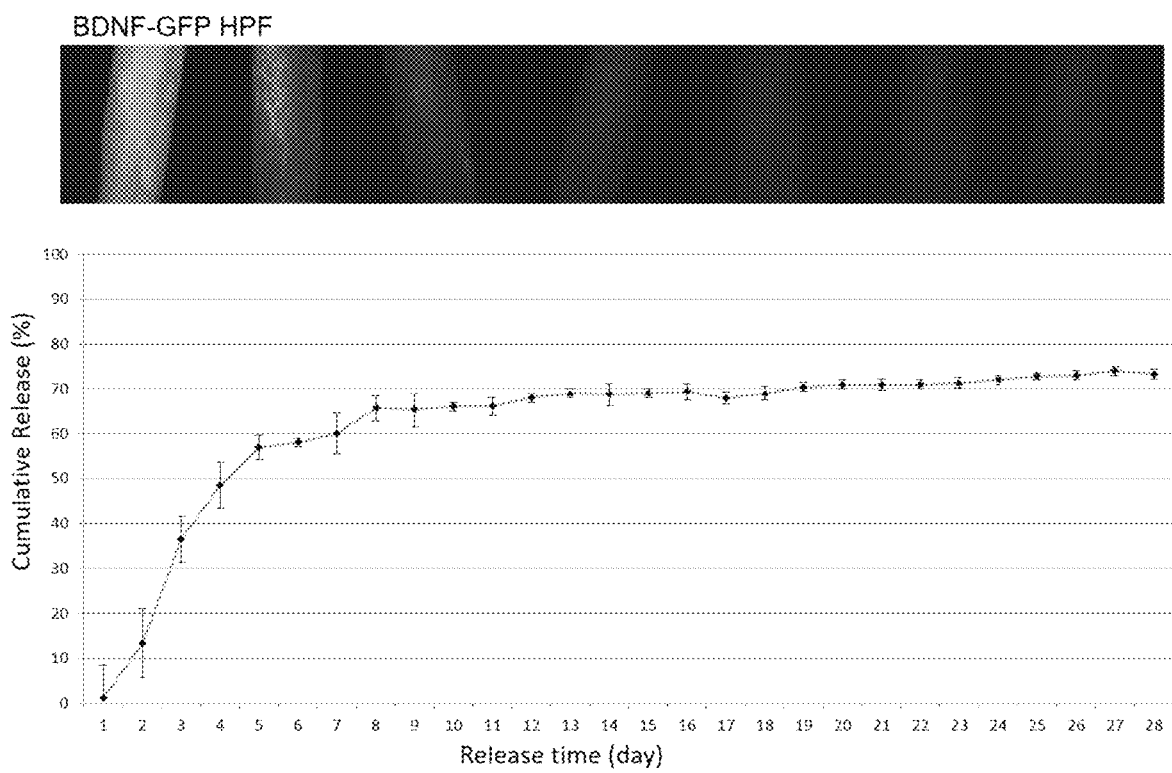
FIG. 14 shows the release behavior of a neurotrophic factor carrier containing the recombinant neurotrophic factor BDNF in vitro for 30 days.
Figure 15:
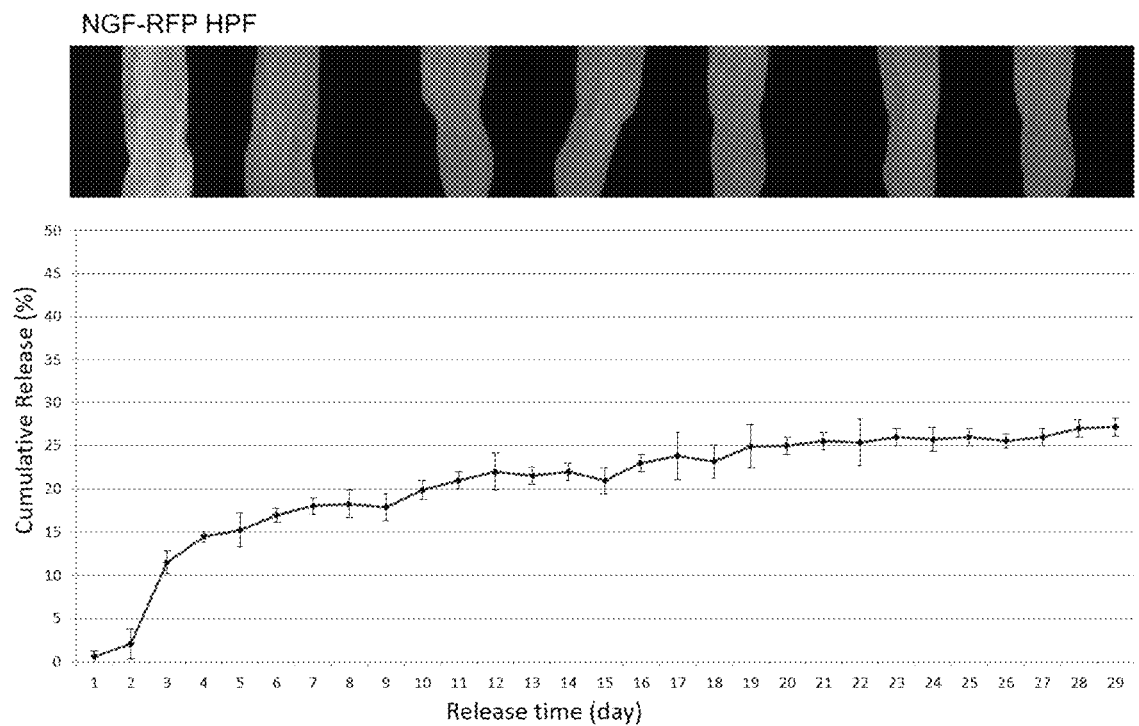
FIG. 15 shows the release behavior of a neurotrophic factor carrier containing the recombinant neurotrophic factor NGF in vitro for 30 days.

As a result, it was confirmed that the recombinant neurotrophic factors BDNF and NGF were released in a sustained manner for over 30 days (FIG. 14 and FIG. 15). In particular, after 3 days, they showed release by diffusion through the microstructure of the nerve conduits. This long-term release behavior for over 30 days is considered effective for nerve regeneration.

The daily release amount was about 3% for BDNF and about 1% for NGF per day. Considering that the initial amount of the neurotrophic factor loaded in the nerve conduit was 1 mg, the neurotrophic factor carrier exhibited a release amount of 10-30 μg per day, which is considered enough for nerve regeneration.

Accordingly, it was confirmed that a large amount of the neurotrophic factor can be coated by adsorbing the protein onto the porous nerve conduit having the microstructure with a large surface area.

Example 4

Confirmation of Nerve Regeneration Effect in Peripheral Nerve Injury Model

A nerve conduit with NGF, as one of NTF, coated on the surface thereof was prepared by the method of Example 1-5.

Then, a polycaprolactone (PCL) tube for inserting the nerve conduit was prepared. The PCL tube was prepared by the following method. A glass tube with an outer diameter of 1.6-1.7 mm was immersed in a 15% (w/v) PCL-TG solution so as to form a thin PCL-TG coat on the surface of the glass tube. Then, the PCL-TG-coated glass tube was immersed in DW, so that the PCL polymer was contacted with the water and then cured and micropores were formed in the hydrophobic polymer as the TG was mixed with the DW and released from the hydrophobic polymer. After removing the glass tube by pushing or pulling with forceps, followed by freezing in liquid nitrogen for 30 seconds and cutting to a length of 18 mm, a PCL tube was completed. The nerve conduit containing NGF was inserted into the PCL tube with a diameter of 1.6-1.7 mm and a length of 18 mm (FIGS. 16A and 16B).

Figure 16:
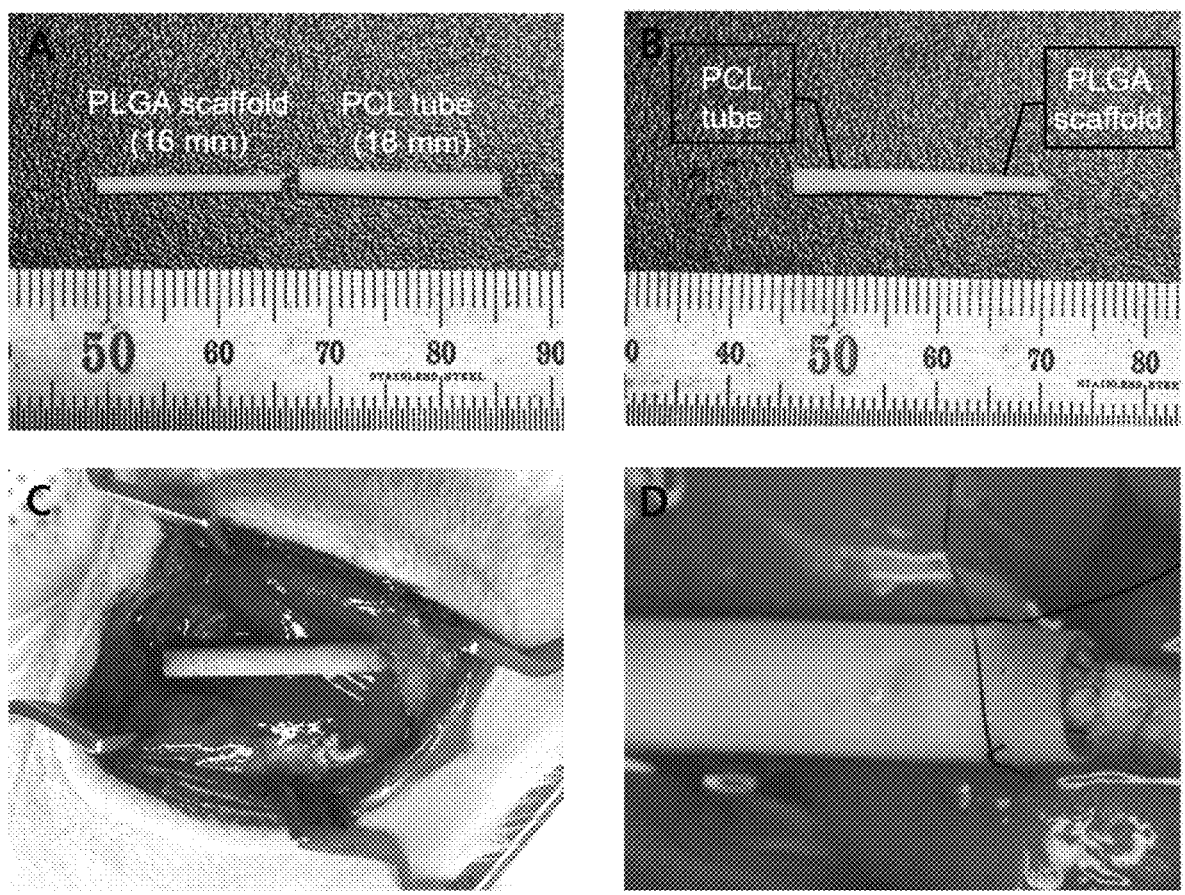
FIG. 16 illustrates an in-vivo experiment procedure for confirming the nerve regeneration effect of a neurotrophic factor carrier according to the present invention in the sciatic nerve. A shows a PCL tube and a PLGA nerve conduit prepared for an in-vivo experiment, B shows an image of a nerve conduit inserted in the PCL tube, and C shows image of a 16-mm nerve conduit inserted after cutting the sciatic nerve of a rat.

After removing the sciatic nerve (length 16 mm) of a 12-week-old female Sprague-Dawley rat at 5 mm below the hip joint, the nerve conduit containing NGF (Scaffold+NGF) or a hollow PCL tube with no nerve conduit inserted (Hollow) or a nerve conduit not containing NGF (Scaffold) as controls was transplanted into the damaged area (FIG. 16C). In order to prevent the nerve conduit from being separated from the nerve, the both ends of the nerve conduit were sutured to the cut nerve terminals using a suture (10-0:0.02-0.029 mm thick nylon suture). As another control group, autografting was conducted after removing the sciatic nerve (length 16 mm) of a 12-week-old female Sprague-Dawley rat at 5 mm below the hip joint. The autografting was conducted by inverting the distal and proximal parts of the cut nerve and suturing with a 10-0 suture (FIG. 16D).

Figure 17:
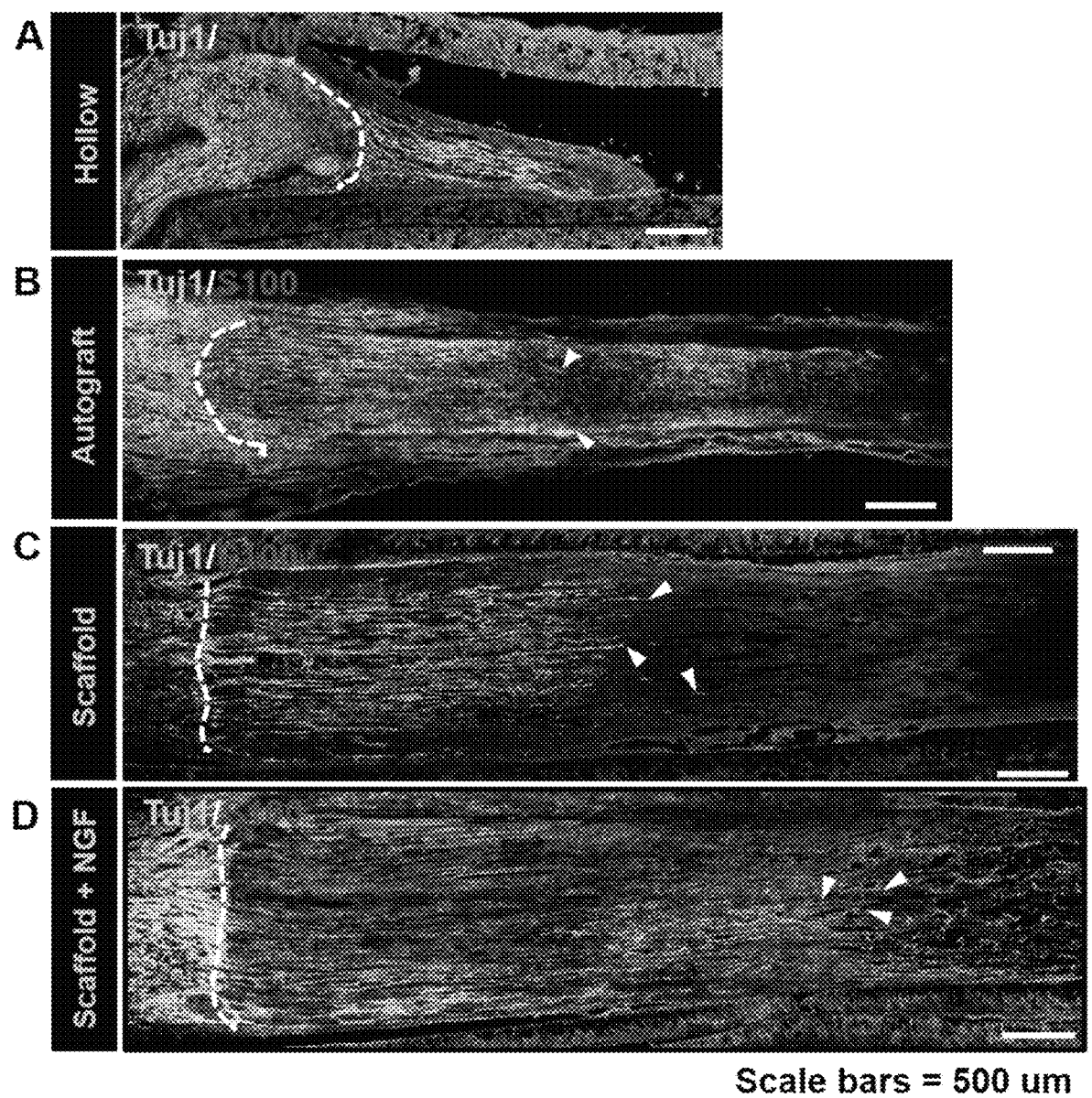
FIG. 17 shows the result of an in-vivo experiment procedure for confirming the nerve regeneration effect of a neurotrophic factor carrier according to the present invention in the sciatic nerve. A shows a tissue into which a hollow PCL tube with no nerve conduit inserted is transplanted (Hollow), B shows an autografted nerve (Autograft), C shows a tissue into which a nerve conduit not containing NGF is transplanted (Scaffold), and D shows a tissue into which a nerve conduit containing NGF is transplanted.

Then, immunostaining was conducted to check the growth of the sciatic nerve. 2 weeks after the transplantation, the sciatic nerve containing the 18-mm long graft was taken out and fixed in 4% paraformaldehyde. Then, after treating with 30% sucrose for 3 days, the tissue was sliced to 16-μm thick sections. Mouse Tuj1 monoclonal antibody was used for staining of the neuronal axons and rabbit S100 polyclonal antibody was used for staining of the Schwann cells. The tissue sections were observed with a confocal microscope and the result is shown in FIG. 17. FIG. 17 shows merged images of mouse Tuj1 monoclonal antibody staining and rabbit S100 polyclonal antibody staining. FIG. 17A shows the tissue into which the hollow PCL tube with no nerve conduit inserted was transplanted (Hollow), FIG. 17B shows the autografted nerve (Autograft), FIG. 17C shows the tissue into which the nerve conduit not containing NGF was transplanted (Scaffold) and FIG. 17D shows the tissue into which the nerve conduit containing NGF was transplanted. More regenerated axons were observed in the tissue into which the nerve conduit containing NGF was transplanted.

Example 5

Confirmation of Nerve Regeneration Effect in Central Nerve Injury (Transection) Model A nerve conduit with NT-3, as one of NTF, coated on the surface thereof was prepared by the method of Example 1-5.

Figure 18:
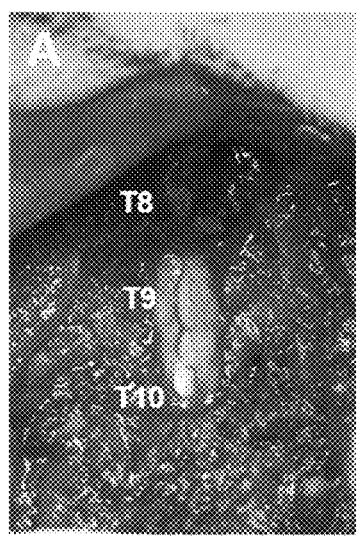
FIG. 18 shows a procedure of inserting a nerve conduit in a complete spinal cord transection model.
Figure 18:
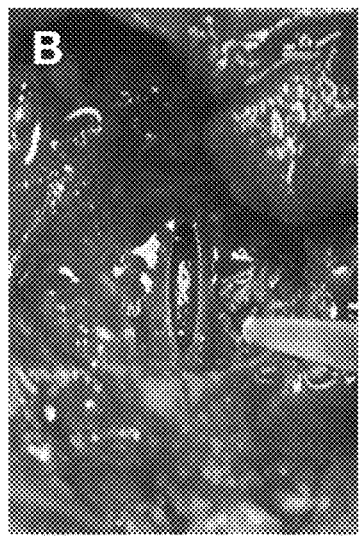
Figure 18:
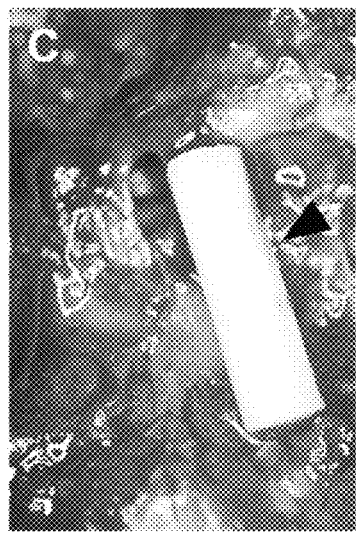
Figure 18:
Figure 18:
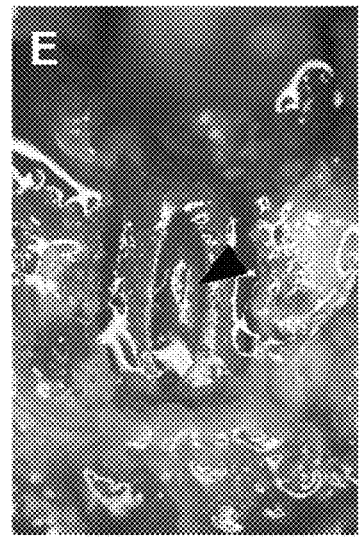
Figure 18:

A central nerve injury model was prepared using a 12-week-old female Sprague-Dawley rat and the nerve conduit was transplanted (FIG. 18). First, laminectomy was conducted on the thoracic vertebrae 9-10 for transplantation of the nerve conduit (FIG. 18A). Then, after cutting open the dura mater of the spinal cord and completely removing the 5-mm long spinal cord (FIG. 18B), the nerve conduit was transplanted into the corresponding area (FIGS. 18C, 18D and 18E). After the nerve conduit transplantation, the dura mater was sutured using a suture (10-0:0.02-0.029 mm thick nylon suture) (FIG. 18F). As a control group, the nerve conduit not containing NT-3 (Scaffold) was transplanted into a spinal cord transection model.

Figure 19:
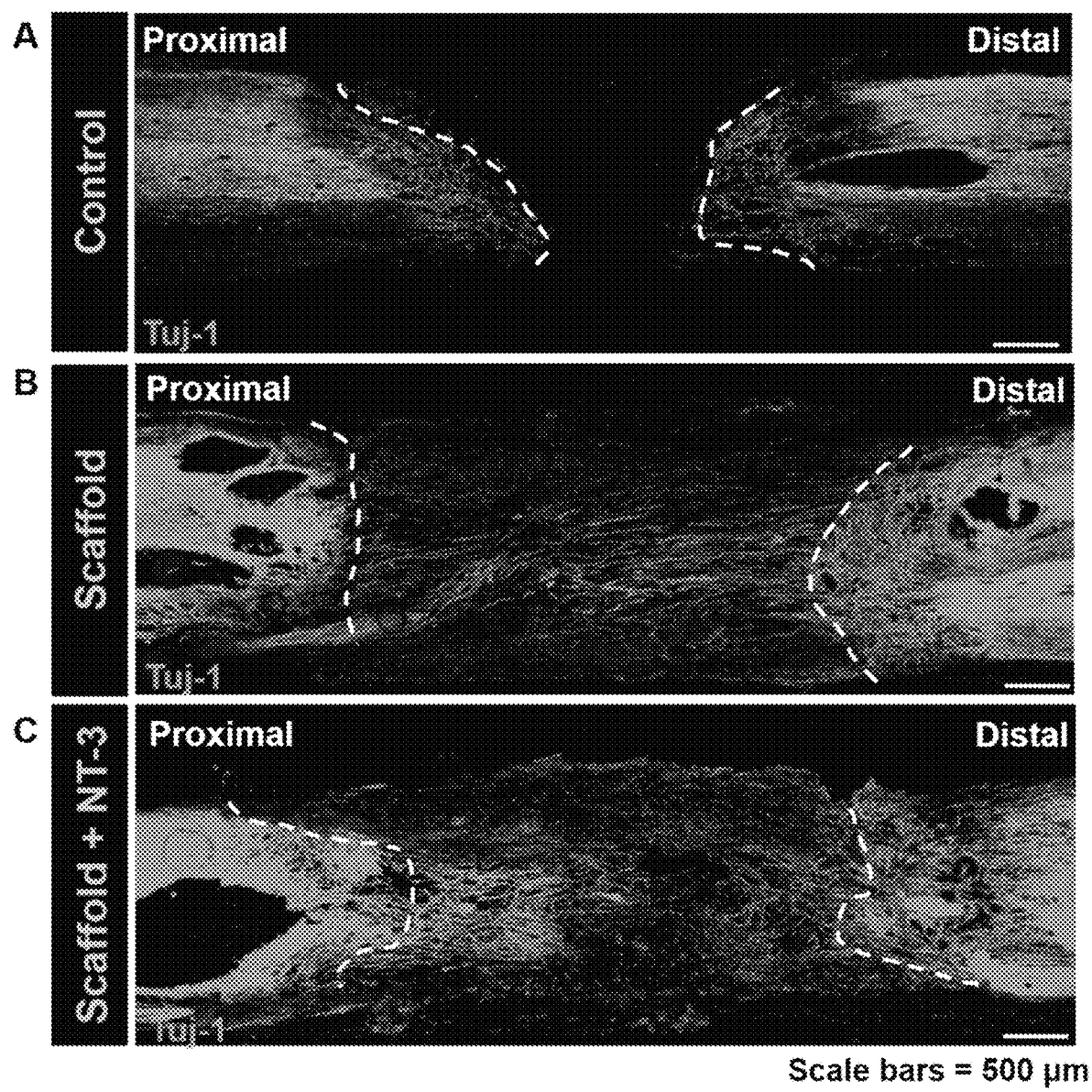
FIG. 19 shows the result of an in-vivo experiment procedure for confirming the nerve regeneration effect of a neurotrophic factor carrier according to the present invention in the spinal cord. A shows a tissue into which a nerve conduit is not transplanted, B shows a tissue into which a nerve conduit not containing NT-3 is transplanted (Scaffold), and C shows a tissue into which a nerve conduit containing NT-3 is transplanted (Scaffold+NT-3).

Then, immunostaining was conducted to check the growth of the central nerve. 16 weeks after the transplantation, the central nerve containing the 5-mm long graft was taken out and fixed in 4% paraformaldehyde. Then, after treating with 30% sucrose for 3 days, the tissue was sliced to 16-μm thick sections. Mouse Tuj1 monoclonal antibody was used for staining of the neuronal axons and the result of confocal microscopic observation is shown in FIG. 19. FIG. 19A shows the tissue into which the nerve conduit was not transplanted, FIG. 19B shows the tissue into which the nerve conduit not containing NT-3 was transplanted (Scaffold) and FIG. 19C shows the tissue into which the nerve conduit containing NT-3 was transplanted (Scaffold+NT-3). More regenerated axons were observed in the tissue into which the nerve conduit containing NT-3 was transplanted.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for preparing a neurotrophic factor carrier including a porous nerve conduit having a microchannel structure with micropores, for regeneration of a central nerve or a peripheral nerve comprising:
   i) preparing a polymer material for a porous nerve conduit having a microchannel structure with micropores, by dissolving a hydrophobic biocompatible polymer of poly(lactic-co-glycolic acid) (PLGA) or polycaprolactone (PCL) in a water-miscible organic solvent of tetraglycol;
   ii) preparing a porous nerve conduit from the polymer material, the nerve conduit having a microchannel structure with micropores,
   iii) immersing the porous nerve conduit in a heparin solution; and
   iv) immersing the porous nerve conduit in a neurotrophic factor solution,
   wherein step ii) comprises:
      inserting a plurality of water-soluble glass fibers into a container having upper and lower channels;
      injecting the polymer material of step i into the container in which the plurality of water-soluble glass fibers are inserted;
      infiltrating the polymer material between the water-soluble glass fibers by applying vacuum to the upper channel;
      separating the water-soluble glass fibers with the polymer material for the porous nerve conduit infiltrated from the container; and
      dissolving the water-soluble glass fibers by immersing the separated glass fibers with the polymer material in water to form the microchannel structure of the hydrophobic polymer,
   wherein in the step of dissolving the water-soluble glass fibers, the microchannels are formed as the hydrophobic biocompatible polymer is cured, and the micropores are formed in the microchannels as the water-miscible organic solvent is mixed with the water and released from the hydrophobic polymer, and
   wherein the polymer material for a nerve conduit is one in which the hydrophobic biocompatible polymer is dissolved in the water-miscible organic solvent at a concentration of 10-40 weight/volume % (w/v %).

2. The method for preparing a neurotrophic factor carrier of claim 1, wherein the neurotrophic factor is selected from a group comprising of NT-3 (neurotrophin-3), NT-4 (neurotrophin-4), BDNF (brain-derived neurotrophic factor), NGF (nerve growth factor), GDNF (glial-derived neurotrophic factor), CNTF (ciliary neurotrophic factor) and a mixture thereof.

3. The method for preparing a neurotrophic factor carrier of claim 2, wherein the neurotrophic factor is a wild-type or recombinant neurotrophic factor.

4. The method for preparing a neurotrophic factor carrier of claim 1, wherein the lower channel has a smaller diameter than the upper channel and the container is sloped with a discontinuous angle.

5. The method for preparing a neurotrophic factor carrier of claim 1, wherein the polymer material for a nerve conduit is in a solution state at room temperature.

6. The method for preparing a neurotrophic factor carrier of claim 1, which further comprises, after the step of dissolving the glass fibers:
  a step of cooling a nerve conduit formed after the glass fibers are dissolved with liquid nitrogen; and
  a step of shaping the cooled nerve conduit by cutting.

7. The method for preparing neurotrophic factor carrier of claim 1, wherein the container is formed of a transparent material so that the infiltration of the polymer material for a nerve conduit can be checked visually.

8. The method for preparing a neurotrophic factor carrier of claim 1, wherein the application of vacuum is repeated multiple times.

* * * * *

SEQUENCE LISTING

<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: human BDNF cDNA forward primer

<400> SEQUENCE: 1
gacggtaccg cacccatggc agaagg    26

<210> SEQ ID NO 2
<211> LENGTH: 25
<212> TYPE: DNA
<213> ORGANISM: Artificial Sequence
<220> FEATURE:
<223> OTHER INFORMATION: human BDNF cDNA reverse primer

<400> SEQUENCE: 2
agaattctca ccgcctcggc ttgtc    25

<210> SEQ ID NO 3
<211> LENGTH: 25
<212> TYPE: DNA
<213> ORGANISM: Artificial Sequence
<220> FEATURE:
<223> OTHER INFORMATION: GFP cDNA forward primer

<400> SEQUENCE: 3
ggaattcgtg agcaagggcg aggag    25

<210> SEQ ID NO 4
<211> LENGTH: 24
<212> TYPE: DNA
<213> ORGANISM: Artificial Sequence
<220> FEATURE:
<223> OTHER INFORMATION: GFP cDNA reverse primer

<400> SEQUENCE: 4
tgaattctac ttgtacagct cgtc    24

<210> SEQ ID NO 5
<211> LENGTH: 23
<212> TYPE: DNA
<213> ORGANISM: Artificial Sequence
<220> FEATURE:
<223> OTHER INFORMATION: human NGF cDNA forward primer

<400> SEQUENCE: 5
ggtaccagca gcagccatcc gat    23

<210> SEQ ID NO 6
<211> LENGTH: 22
<212> TYPE: DNA
<213> ORGANISM: Artificial Sequence
<220> FEATURE:
<223> OTHER INFORMATION: human NGF cDNA reverse primer

<400> SEQUENCE: 6
gaattcgccg cacgacgcac cg    22

<210> SEQ ID NO 7
<211> LENGTH: 31
<212> TYPE: DNA
<213> ORGANISM: Artificial Sequence
<220> FEATURE:
<223> OTHER INFORMATION: RFP cDNA forward primer

<400> SEQUENCE: 7
aagcttaatt aattaagttt gtgccccagt t    31

<210> SEQ ID NO 8
<211> LENGTH: 30
<212> TYPE: DNA
<213> ORGANISM: Artificial Sequence
<220> FEATURE:
<223> OTHER INFORMATION: RFP cDNA reverse primer

```
<400> SEQUENCE: 8
aagcttaatt aagtttgtgc cccagtttgc                                    30

<210> SEQ ID NO 9
<211> LENGTH: 27
<212> TYPE: DNA
<213> ORGANISM: Artificial Sequence
<220> FEATURE:
<223> OTHER INFORMATION: human GDNF cDNA forward primer

<400> SEQUENCE: 9
ggtaccagtc cggataaaca aatggca                                       27

<210> SEQ ID NO 10
<211> LENGTH: 28
<212> TYPE: DNA
<213> ORGANISM: Artificial Sequence
<220> FEATURE:
<223> OTHER INFORMATION: human GDNF cDNA reverse primer

<400> SEQUENCE: 10
gaattcaata caaccacaac gttttgcg                                      28

<210> SEQ ID NO 11
<211> LENGTH: 27
<212> TYPE: DNA
<213> ORGANISM: Artificial Sequence
<220> FEATURE:
<223> OTHER INFORMATION: human CNTF cDNA forward primer

<400> SEQUENCE: 11
ggtaccgcat ttaccgaaca tagtccg                                       27

<210> SEQ ID NO 12
<211> LENGTH: 34
<212> TYPE: DNA
<213> ORGANISM: Artificial Sequence
<220> FEATURE:
<223> OTHER INFORMATION: human CNTF cDNA reverse primer

<400> SEQUENCE: 12
gaattccatt tttttgttgt tggcaatata atgg                               34
```